United States Patent [19]

Eaton

[11] 4,336,056
[45] Jun. 22, 1982

[54] HERBICIDAL METHOD FOR FALLOW LAND
[75] Inventor: Benny J. Eaton, Greenfield, Ind.
[73] Assignee: Eli Lilly and Company, Indianapolis, Ind.
[21] Appl. No.: 135,753
[22] Filed: Mar. 31, 1980
[51] Int. Cl.$^3$ ............................................. A01N 43/00
[52] U.S. Cl. ........................................... 71/88; 71/93; 71/94
[58] Field of Search ...................................... 71/88, 90
[56] References Cited
U.S. PATENT DOCUMENTS

| | | | |
|---|---|---|---|
| 2,535,876 | 12/1950 | Stewart | 71/90 |
| 3,301,832 | 1/1967 | D'Amico | 71/90 |
| 3,458,305 | 7/1969 | Doyle | 71/90 |
| 3,972,706 | 8/1976 | Arnold | 71/88 |
| 4,062,861 | 12/1977 | Yukinaga et al. | 71/88 |

OTHER PUBLICATIONS

Miller "Herbicides Spring Applied & Fall Applied, etc", (1979) Res. Rept. N.C. Weed Control Conf. 36 pp. 71–73.
Stahlman, "Weed Control During Fallow etc", (1979) Res. Rept. N.C. Weed Control Conf. 36 pp. 66–67.

Primary Examiner—Glennon H. Hollrah
Attorney, Agent, or Firm—Charles W. Ashbrook; Arthur R. Whale

[57] ABSTRACT

A method for controlling unwanted vegetation in fallow land, particularly in fallow wheatland, employing a 3-isoxazolylurea herbicide is described.

2 Claims, No Drawings

HERBICIDAL METHOD FOR FALLOW LAND

BACKGROUND OF THE INVENTION

Wheat, corn, oats, barley and related grains are major crops raised for both human and animal consumption. Such crops are becoming increasingly important energy sources. Since the amount of world-wide grain production becomes more critical as total population expands and as natural energy sources diminish, novel methods for increasing crop yields are constantly being sought.

One of the major problems with growing grain crops in certain sections of the world is the lack of sufficient water. Irrigation in such areas generally is impossible, and total yearly rainfall is customarily insufficient in such areas to permit the growing of crops every year on the same land. Accordingly, one practice commonly followed in areas receiving a sparcity of rainfall is to allow the land to lie fallow during alternate years. The practice of a fallow land program requires that the land remain unplanted during the year following the harvest of a crop. Such practice permits the accumulation and conservation of the available soil moisture, and thus permits the growth of a grain crop in the growing season following the fallow period.

One of the primary problems with fallow land programs is the growth of unwanted vegetation during the fallow period. Such growth of weeds and grasses robs the soil of the moisture and nutrients needed for later crop growth. Moreover, if the weeds are permitted to reach maturity, the seeds are spread by natural means so that the growth of unwanted vegetation is extended both in area and in population.

The conventional method for controlling the growth of unwanted vegetation in fallow land has been to till the soil periodically during the fallow period. This method of vegetative control suffers from numerous drawbacks. Effective tillage control requires repeated passages over the soil, for example up to about five or more such passages during the fallow period. Such repeated operations with conventional fuel consuming equipment is becoming more and more impractical economically. Moreover, such repeated operations require the investment of substantial man-hours. Additionally, soil cultivation opens the soil, thus permitting the escape of soil moisture by evaporation, as well as permitting erosion of the loose soil due to wind.

While a large number of chemical herbicides are now known which are effective in controlling the growth of a wide variety of broadleaf and grassy weeds, their use in a fallow land program generally is precluded for any of a number of reasons. Many such herbicides are not sufficiently long lasting to provide effective control during an entire fallow period. Other herbicides have a substantial carry-over such that desired crops are injured during the growing season following the fallow period.

A herbicide, to be effective in a fallow land program, must meet several requirements:

1. The herbicide should be active both as a preemergence and as a postemergence herbicide. Thus, the herbicide should be active against the weeds which are already growing at the time of crop harvest, for instance those weeds growing in the stubble of the wheat at the time the wheat is harvested. Additionally, the herbicide should be active against the weeds which sprout and come up after the herbicide has been applied.

2. The herbicide should have a broad spectrum of activity. For example, in a fallow wheatland program, a herbicide should be capable of controlling volunteer wheat, in addition to the annual grass and broadleaf weeds which occur in the wheat fields, both immediately after the winter wheat has been harvested, and in the following spring and summer of the fallow period before the soil is prepared and the planting of the next crop of wheat occurs.

3. The herbicide should not be bound to plant residues. For example, in a fallow wheatland program, a herbicide is best applied as a spray over the remaining wheat stubble and wheat straw after the harvest of the crop of wheat, and in order to have greatest utility, the herbicide should permit itself to be washed off of the wheat stubble and wheat straw and other plant residues by the light showers which provide the moisture during the fallow period. By being washed off of the plant residues, the herbicide becomes available for action in the soil where weeds and volunteer wheat sprout and emerge.

4. The herbicide should be stable on soil surfaces and not sensitive to light. Some herbicides are very sensitive to light and therefore, when sprayed over crop residues such as wheat stubble or upon a soil surface and exposed to sunlight, decompose in a very short period of time, a matter of a week or so. The herbicide should be stable on the soil surface so that it is available for action against the later-emerging weeds and volunteer crop such as wheat.

5. The herbicide should be one which is activated with small amounts of rainfall. Because rainfall is so scarce in the regions where a fallow program is practiced, every small amount of moisture is important. If a herbicide is used which requires large amounts of water, for instance an inch or more of rain, to be activated, months could go by before sufficient moisture accumulates to effect activation of the herbicide. In the meantime, weeds and volunteer crop such as wheat could sprout and grow completely out of control. It is therefore important that the herbicide be activated with a small amount of moisture such as one inch or less of rainfall in order to eliminate the weeds and volunteer crop.

6. The activity of the herbicide should not be altered by tillage. This characteristic is important because, depending on the method of practicing the fallow rotation method, the farmer may occasionally wish to cultivate the soil during the fallow year, but it is desirable that the herbicide continue to work to control any weeds which remain or which begin to sprout, which in so doing will remove moisture from the soil. A herbicide which will continue to work after it has been incorporated into the soil in this manner is a desirable product to use.

7. The herbicide should provide approximately a year, that is to say about 10 to 12 months, of weed control in order to be a satisfactory herbicide for use in this fallow land rotation method. This figure is arrived at by considering that a crop such as wheat is usually harvested in July or August, and immediately thereafter the herbicide is applied. To be a satisfactory and suitable herbicide for use in this method, the herbicide should exert its influence on the weeds which were growing at the time the herbicide was applied in late July or in August, and continue to function as a herbicide throughout the remainder of the summer and fall until cold weather comes. Then in the following spring when the earth warms up and the weeds again begin to sprout, along with volunteer wheat and the like, the herbicide should continue to act, and its activity should continue through the spring and summer months up until time to prepare the soil and plant the crop seed for the new crop. For a fallow wheatland program, this period is approximately 10 to 12 months or so from the date at which the herbicide was originally applied.

8. The herbicide should be one which will undergo sufficient degradation to ensure adequate crop tolerance at the end of the fallow period. Thus, the ideal herbicide is one which will last for an extended period of time, say in the vicinity of 10 or 12 months, but, at the end of that time, will have degraded to an extent that it is harmless to the new crop. A herbicide which has not degraded by the end of this long period of time during which the land remains fallow will damage the new crop and decrease the yield thereof, and this is undesirable.

An object of this invention is to provide a method of weed control in fallow land which accomplishes substantially all of the objectives of a chemical fallow program. The method is directed particularly to a fallow wheatland program.

SUMMARY OF THE INVENTION

This invention concerns a method for controlling unwanted vegetation in fallow land. More particularly, this invention provides a herbicidal method for killing and preventing the growth of unwanted vegetation on fallow land comprising applying to the locus of the fallow land to be treated a herbicidally-effective amount of a 3-isoxazolylurea herbicide derivative selected from the group of herbicidal compounds disclosed in U.S. Pat. No. 4,062,861. A preferred method comprises applying a 3-isoxazolylurea herbicide to fallow wheatland. A further preferred method according to this invention comprises applying a 3-isoxazolylurea of the formula

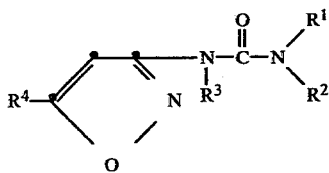

wherein:
$R^1$ is hydrogen or $C_1-C_4$ alkyl;
$R^2$ is $C_1-C_4$ alkyl, $C_1-C_4$ alkoxy, $C_2-C_4$ alkenyl or $C_1-C_4$ alkylthio;
$R^3$ is hydrogen or $C_1-C_4$ alkyl; and
$R^4$ is $C_1-C_6$ alkyl.

An additionally preferred herbicidal method according to this invention comprises applying to fallow wheatland a herbicidally effective amount of a compound of the above formula wherein $R^1$ and $R^2$ independently are $C_1-C_4$ alkyl, $R^3$ is hydrogen and $R^4$ is $C_1-C_4$ alkyl.

A more preferred method of this invention comprises applying to the locus to be treated an effective amount of a 3-isoxazolylurea derivative selected from:
1-methyl-3-(5-isopropyl-3-isoxazolyl)urea;
1-methyl-3-(5-tert.-butyl-3-isoxazolyl)urea;
1,1-dimethyl-3-(5-tert.-butyl-3-isoxazolyl)urea;
1,3-dimethyl-3-(5-tert.-butyl-3-isoxazolyl)urea;
1,1,3-trimethyl-3-(5-tert.-butyl-3-isoxazolyl)urea;
1-methyl-1-butyl-3-(5-tert.-butyl-3-isoxazolyl)urea;
1-allyl-1-methyl-3-(5-tert.butyl-3-isoxazolyl)urea;
1,1-dimethyl-3-(5-isopropyl-3-isoxazolyl)urea;
1-methoxy-1-methyl-3-(5-tert.-butyl-3-isoxazolyl)urea;
1-butylthio-1-methyl-3-(5-tert.-butyl-3-isoxazolyl)urea;
1-methyl-1-butyl-3-(5-isopropyl-3-isoxazolyl)urea;
1,3-dimethyl-3-(5-isopropyl-3-isoxazolyl)urea;
and related isoxazolyl ureas.

The most preferred herbicidal method of this invention comprises applying to fallow wheatland an effective amount of 1,1-dimethyl-3-(5-tert.-butyl-3-isoxazolyl)urea.

DETAILED DESCRIPTION OF THE INVENTION

The novel herbicidal method provided by this invention is practiced by applying to fallow land, particularly to fallow wheatland, a herbicidally effective amount of a 3-isoxazolylurea derivative selected from those herbicidial 3-isoxazolylureas disclosed in U.S. Pat. No. 4,062,861. Preferred 3-isoxazolylurea derivatives to be utilized according to this invention have the above general formula. As noted above, $R^1$ in the above formula defines hydrogen or $C_1-C_4$ alkyl such as methyl, ethyl, n-propyl, isopropyl, n-butyl, tert.-butyl and the like. $R^2$ in the above formula similarly defines a $C_1-C_4$ alkyl group, as well as a $C_1-C_4$ alkoxy group such as methoxy, ethoxy, n-propoxy, n-butoxy, sec-butoxy, and the like, $C_2-C_4$ alkenyl such as allyl and 3-butenyl, and $C_1-C_4$ alkylthio such as methylthio, n-butylthio, and the like. $R^3$ in the above formula represents hydrogen or $C_1-C_4$ alkyl, and $R^4$ defines a $C_1-C_6$ alkyl moiety such as methyl, ethyl, n-propyl, isopropyl, n-pentyl, 2-methylpentyl, n-hexyl, tert.-butyl, and related groups.

An especially preferred method comprises applying a herbicidally-effective amount of 1,1-dimethyl-3-(5-tert.-butyl-3-isoxazolyl)urea to fallow wheatland following wheat harvest.

The herbicidal method provided by this invention is practiced by applying a herbicidally-effective amount of a 3-isoxazolylurea derivative to fallow land, preferably to fallow wheatland, although the method can be practiced on fallow cornland, fallow sorghum land, and similar fallow lands. The 3-isoxazolylurea herbicide generally is applied to the fallow land soon after the crop is harvested, for instance within about one to about thirty days following harvest. This early application is preferred in the case of wheatland and oatland, since such crops are harvested in July, August, or September, and sufficient growing season remains to allow unwanted vegetation to germinate and grow. In all such cases, the herbicide can be applied preemergence or early postemergence to the weeds, for example within about one to about two weeks postemergence, generally before the weed seedlings are more than about two inches high.

The particular rate of application of a 3-isoxazolylurea will of course be determined in part by a consideration of several factors, including the expected population of unwanted vegetation, the soil texture and composition, the particular herbicide compound applied, the method of application, the subsequent climate, and related factors. Typically, application of a 3-isoxazolylurea such as 1,1-dimethyl-3-(5-tert.-butyl-3-isoxazolyl)urea at a rate of about 0.3 to about 3.0 kg/ha will be effective to control most or all of the broadleaf and grassy weeds commonly encountered in land permitted to remain fallow. A preferred rate of application is about 0.4 to about 1.5 kg/ha.

The 3-isoxazolylureas to be utilized according to this invention can be formulated according to routine methods with any of several known and commonly used herbicidal diluents, adjuvants and carriers. If desired, those urea derivatives with at least one active hydrogen can be converted to an alkali metal or alkaline earth metal salt, thereby facilitating formulation in solvents such as water. The formulations can contain liquid carriers and adjuvants such as organic solvents, including benzene, xylene, ortho-chlorotoluene, n-hexane, and the like, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders or aqueous emulsifiable concentrates which can be diluted with water at the site of application. Also preferred are formulations as granules, dusts, and the like, which can be applied in the dry state.

When desired, the 3-isoxazolylureas can be applied in combination with other herbicidal agents in an effort to achieve even broader vegetative control. Typical herbicides which can be conveniently combined with the 3-isoxazolylureas include atrazine, hexazinone, metribuzin, ametryn, cyanazine, cyprazine, prometon, prometryn, propazine, simazine, terbutryn, and related herbicides.

An especially preferred combination to be utilized for the herbicidal control of weeds in fallow wheatland comprises 1,1-dimethyl-3-(5-tert.-butyl-3-isoxazolyl)urea and 2-ethylamino-4-isopropylamino-6-chloro-s-triazine, commonly referred to as atrazine. Such preferred herbicides can be formulated together, or alternatively can be combined at the site of application, for instance by tank mixing or the like. Typically, such combination will be comprised of about one part by weight of the urea and about one part by weight of atrazine. A customary rate of application of such combination will be about 0.4 to about 0.6 kg/ha of the urea and about 0.4 to about 0.6 kg/ha of atrazine.

Another preferred combination to be used in the method of this invention comprises a 3-isoxazolylurea and a total kill contact herbicide such as paraquat. Such combination is particularly useful when the land to be treated contains weeds having extended post-emergent growth.

The herbicides contemplated herein can be applied by any of several methods according to this invention. Generally, the compounds will be surface applied as an aqueous spray. Such application can be carried out by conventional ground equipment, or if desired the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means, although this permits moisture evaporation and lessens the effectiveness of the overall chemical fallow program.

The herbicidal method of this invention is effective in the control of a wide variety of broadleaf and grassy weeds. Typical of the various species of vegetative growth to be controlled, combated, or eliminated are: annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials commonly controlled include wild barley, campion, burdock, bull thistle, roundleaved mallow, purple star thistle, and the like. Also controlled by the present method are perennials such as quackgrass, Johnson grass, canada thistle, curly dock, field chickweed, dandelion, Russian knapweed, aster, horetail, ironweed, sesbania, cattail, wintercress, horsenettle, nutsedge, milkweed, sicklepod, and the like.

The herbicidal method for fallow land provided by this invention has been demonstrated efficacious in open field tests conducted in summer fallow wheatland in several western states having a sparcity of rainfall, such as Kansas, Colorado and Nebraska, as well as in various dry regions of Canada. In a typical experiment, a 3-isoxazolylurea herbicide was surface applied as an aqueous spray at various concentrations to wheat stubble within about three weeks following harvest. The wheat stubble was about 15 to about 18 inches tall. Applications were made to plots measuring about 15 feet by about 50 feet. In each test, the soil was flat with no clods. The moisture was supplied only by natural rainfall following application by aqueous spray. Herbicidal applications were accomplished by a conventional tractor mounted sprayer having a spray width of fifteen feet. Ground speed was three miles per hour, with an operating pressure of 27 psi, thus delivering 25 gallons of aqueous spray per acre. The experiments were a randomized complete block with three replications for each application rate. Percent weed control ratings were made at various intervals up to one year following initial application of herbicide. Control plots received no herbicide.

The results of one such study are presented in Table 1. The field test was carried out near Sidney, Nebraska, with a loam soil texture, and 2.6 percent organic content. The herbicide evaluated was 1,1-dimethyl-3-(5-tert.-butyl-3-isoxazolyl)urea.

TABLE 1

| Weed Species | Application rate Pounds/acre | Percent Weed Control |
|---|---|---|
| Common Lambsquarters | 0.75 | 86.7[a] |
|  | 0.75 | 100.0[b] |
|  | 1.5 | 98.3[a] |
|  | 1.5 | 100.0[b] |
| Sunflower | 0.75 | 73.3[a] |
|  | 1.5 | 81.7[a] |
| Kochia | 0.75 | 100.0[a] |
|  | 1.5 | 100.0[a] |
| Wild Buckwheat | 0.75 | 60.0[a] |
|  | 0.75 | 100.0[b] |
|  | 1.5 | 78.3[a] |
|  | 1.5 | 100.0[b] |
| Smartweed | 0.75 | 100[b] |
|  | 1.5 | 100[b] |
| Russian Thistle | 0.75 | 46.7[a] |
|  | 0.75 | 99.7[b] |
|  | 1.5 | 60.0[a] |
|  | 1.5 | 100.0[b] |
| Volunteer wheat | 0.75 | 100.0[b] |
|  | 1.5 | 100.0[b] |

[a] observation made 14 days post application
[b] observation made 282 days post application A similar test was carried out near Goodland, Kansas, on silt loam soil having an organic content of 2.7 percent. The herbicide tested was 1,1-dimethyl-3-(5-tert.-butyl-3-isoxazolyl)urea. The results are presented in Table 2.

TABLE 2

| Weed Species | Application rate Pounds/acre | Percent Weed Control |
|---|---|---|
| Common Lambsquarters | 0.75 | 100.0[a] |
|  | 1.5 | 100.0[a] |
| Sunflower | 0.75 | 100.0[a] |
|  | 1.5 | 100.0[a] |
| Kochia | 0.75 | 100.0[a] |
|  | 1.5 | 100.0[a] |
| Witchgrass | 0.75 | 76.7[b] |
|  | 0.75 | 73.3[c] |
|  | 0.75 | 100.0[d] |
|  | 1.5 | 92.0[b] |
|  | 1.5 | 86.7[c] |
|  | 1.5 | 100.0[d] |
| Russian Thistle | 0.75 | 45.0[b] |
|  | 0.75 | 40.0[c] |
|  | 0.75 | 100.0[d] |
|  | 0.75 | 99.3[a] |
|  | 1.5 | 65.0[b] |
|  | 1.5 | 73.3[c] |
|  | 1.5 | 100.0[d] |
|  | 1.5 | 100.0[a] |
| Buffalobur | 0.75 | 84.0[b] |
|  | 0.75 | 73.3[c] |
|  | 1.5 | 96.7[b] |
|  | 1.5 | 92.3[c] |
| Volunteer Wheat | 0.75 | 40.0[b] |
|  | 0.75 | 66.7[c] |
|  | 0.75 | 100.0[d] |
|  | 0.75 | 99.3[a] |
|  | 1.5 | 76.7[b] |
|  | 1.5 | 70.0[c] |
|  | 1.5 | 100.0[d] |
|  | 1.5 | 100.0[a] |

[a] observation made 300 days post treatment.
[b] observation made 20 days post treatment.
[c] observation made 34 days post treatment.
[d] observation made 286 days post treatment.

A similar test was carried out on sandy clay loam near Otis, Colo. The soil had an organic content of 1.9 percent. The efficacy of 1,1-dimethyl-3-(5-tert.-butyl-3-isoxazolyl)urea is reported in Table 3.

TABLE 3

| Weed Species | Application rate Pounds/acre | Percent Weed Control |
|---|---|---|
| Common Lambsquarters | 0.75 | 100.0[a] |
|  | 0.75 | 100.0[b] |
|  | 1.5 | 100.0[a] |
|  | 1.5 | 100.0[b] |
| Stinkgrass | 0.75 | 75.0[a] |
|  | 1.5 | 97.3[a] |
| Kochia | 0.75 | 94.3[a] |
|  | 0.75 | 100.0[b] |
|  | 0.75 | 100.0[c] |
|  | 1.5 | 100.0[a] |
|  | 1.5 | 100.0[b] |
|  | 1.5 | 100.0[c] |
| Common Purslane | 0.75 | 100.0[a] |
|  | 1.5 | 100.0[a] |
| Russian Thistle | 0.75 | 95.7[a] |
|  | 0.75 | 100.0[b] |
|  | 0.75 | 100.0[c] |
|  | 1.5 | 100.0[a] |
|  | 1.5 | 100.0[b] |
|  | 1.5 | 100.0[c] |
| Volunteer wheat | 0.75 | 100.0[b] |
|  | 0.75 | 99.3[c] |
|  | 1.5 | 100.0[b] |

TABLE 3-continued

| Weed Species | Application rate Pounds/acre | Percent Weed Control |
|---|---|---|
|  | 1.5 | 99.7[c] |

[a] observation 32 days post application
[b] observation 283 days post application
[c] observation 300 days post application An aqueous solution of 1,1-dimethyl-3-(5-tert.-butyl-3-isolazolyl)urea was surface applied as a spray to sandy loam soil near Lyleton, Manatoba, Canada. The herbicidal affects of the compound as a fallow wheatland herbicide were analyzed 266 days post application. The results are presented in Table 4.

TABLE 4

| Weed Species | Application rate kg/ha | Percent Weed Control |
|---|---|---|
| Common Lambsquarters | 0.5 | 100.0 |
|  | 0.75 | 100.0 |
| Flixweed | 0.5 | 100.0 |
|  | 0.75 | 100.0 |
| Green Foxtail | 0.5 | 80.0 |
|  | 0.75 | 90.0 |
| Russian Thistle | 0.5 | 93.3 |
|  | 0.75 | 96.7 |

The data presented in Tables 1-4 demonstrate the usefulness of 3-isoxazolylureas in a chemical fallow land program.

The following detailed examples are provided by way of illustration of specific aspects of the invention.

EXAMPLE 1

1,1-Dimethyl-3-(5-tert.-butyl-3-isoxazolyl)urea is prepared by condensing dimethylamine with 5-tert.-butyl-3-isoxazolyl isocyanate in benzene. After removal of the reaction solvent and purification by chromatography or crystallization, there is obtained 1,1-dimethyl-3-(5-tert.-butyl-3-isoxazolyl)urea. M.P. 119.5°–120.5° C.

EXAMPLES 2–12

The following 3-isoxazolylurea herbicides are to be utilized in the method of this invention and are prepared according to the method of Example 1.
1-methyl-3-(5-isopropyl-3-isoxazolyl)urea;
1-methyl-3-(5-tert.-butyl-3-isoxazolyl)urea;
1,3-dimethyl-3-(5-tert.-butyl-3-isoxazolyl)urea;
1,1,3-trimethyl-3-(5-tert.-butyl-3-isoxazolyl)urea;
1-methyl-1-butyl-3-(5-tert.-butyl-3-isoxazolyl)urea;
1-allyl-1-methyl-3-(5-tert.-butyl-3-isoxazolyl)urea;
1,1-dimethyl-3-(5-isopropyl-3-isoxazolyl)urea;
1-methoxy-1-methyl-3-(5-tert.-butyl-3-isoxazolyl)urea;
1-butylthio-1-methyl-3-(5-tert.-butyl-3-isoxazolyl)urea;
1-methyl-1-butyl-3-(5-isopropyl-3-isoxazolyl)urea;
1,3-dimethyl-3-(5-isopropyl-3-isoxazolyl)urea

EXAMPLE 13

| Formulation of Wettable Powder | |
|---|---|
| Ingredient | Percent by weight |
| 1,1-dimethyl-3-(5-tert.-butyl-3-isoxazolyl)urea | 80.0 |
| wetting agent (Tergital TMN) | 2.0 |
| fumed silica (HiSil) | 18.0 |

| Formulation of Wettable Powder | |
| --- | --- |
| Ingredient | Percent by weight |
| | 100.0 |

The 3-isoxazolylurea herbicide is added to a uniform dry mixture of Tergital TMN and HiSil. The Tergital TMN is a commercial trimethyl nonane derivative of an α-(p-dodecylphenyl)-ω-hydroxypoly(oxyethylene), which is a nonionic wetting agent adjuvant. Other commonly used adjuvants include the albenates, non-oxynols, octoxynols, oxysorbics, and the like. The HiSil is a commercial form of fumed silicon dioxide, which is used as a carrier and geling agent. Once the 3-isoxazolylurea and the adjuvant are mixed to uniformity, the powder can be ground through a hammer mill to provide an 80 percent by weight wettable powder. The powder can be added to water and applied to wheat stubble at the rate of about 0.5 to about 2.0 pounds of active ingredient per acre.

EXAMPLE 14

Tank Mix Formulation

A wettable powder formulation containing about 75 percent by weight of 1,1-dimethyl-3-(5-tert.-butyl-3-isoxazolyl)urea is added to an aqueous mixture of a liquid formulation of atrazine (four pounds per gallon). The final formulation comprises about 1.5 pounds of the 3-isoxazolylurea and about 1.5 pounds of atrazine per about 30 gallons of aqueous mixture. The tank mixed aqueous formulation is surface applied to wheat stubble at the rate of about 30 gallons per acre for the effective control of unwanted vegetation such as foxtail and morningglory for about one year.

The treated fallow land can be seeded with a new crop such as wheat following the fallow period. The herbicide is sufficiently degraded so that no adverse affects on the growth or yield of the new crop are observed which are attributable to the herbicide used in the chemical fallow program.

I claim:

1. A method for killing and controlling the growth of unwanted vegetation on follow wheatland between the time of harvesting the wheat crop and the time of the next planting of winter wheat which method comprises applying to the locus where vegetative control is desired a herbicidally-effective amount of a 1,1-dimethyl-3-(5-tert-butyl-3-isoxazolyl)urea.

2. The method of claim 1 employing the active agent at a rate of about 0.3 to about 3.0 Kg./ha.

* * * * *